(12) United States Patent
Niemeyer

(10) Patent No.: US 7,750,202 B2
(45) Date of Patent: *Jul. 6, 2010

(54) DISPOSABLE ABSORBENT ARTICLE HAVING INTERACTIVE GRAPHICS

(75) Inventor: Michael J. Niemeyer, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 973 days.

This patent is subject to a terminal disclaimer.

(21) Appl. No.: 11/026,896

(22) Filed: Dec. 30, 2004

(65) Prior Publication Data

US 2006/0149197 A1    Jul. 6, 2006

(51) Int. Cl.
*A61F 13/15* (2006.01)

(52) U.S. Cl. .................. 604/361; 604/367; 604/366

(58) Field of Classification Search .............. 604/361, 604/367, 366
See application file for complete search history.

(56) References Cited

U.S. PATENT DOCUMENTS

| | | | |
|---|---|---|---|
| 2,681,032 A | 6/1954 | Shaw | |
| 4,834,733 A | 5/1989 | Huntoon et al. | |
| 5,527,303 A | 6/1996 | Milby, Jr. et al. | |
| 5,797,892 A | 8/1998 | Glaug et al. | |
| 6,162,961 A | 12/2000 | Tanner et al. | |
| 6,217,563 B1 | 4/2001 | Van Gompel et al. | |
| 6,297,424 B1 * | 10/2001 | Olson et al. | 604/361 |
| 6,307,119 B1 | 10/2001 | Cammarota et al. | |
| 6,352,528 B1 | 3/2002 | Weber et al. | |
| 6,362,389 B1 | 3/2002 | Mcdowall et al. | |
| 6,514,187 B2 | 2/2003 | Coenen et al. | |
| 6,562,167 B2 | 5/2003 | Coenen et al. | |
| 6,596,918 B1 | 7/2003 | Wehrle et al. | |

(Continued)

FOREIGN PATENT DOCUMENTS

EP     0 226 789 A2     7/1987

(Continued)

OTHER PUBLICATIONS

American Society for Testing Materials (ASTM) Designation: D1921-01, "Standard Test Methods for Particle Size (Sieve Analysis) of Plastic Materials," pp. 1-5, published Oct. 2001.

*Primary Examiner*—Jacqueline F. Stephens
(74) *Attorney, Agent, or Firm*—Denise L. Stoker; Randall W. Fieldhack

(57) ABSTRACT

A disposable absorbent article having improved interactive graphics is disclosed. The disposable absorbent article defines a front waist end, a back waist end, and a length which extends between the front and back waist ends. In particular embodiments, the article includes an active graphic disposed on the bodyside liner and/or outer cover, and the active graphic is positioned within one of a frontmost 30% and a backmost 30% of the article's length. In particular embodiments, the article includes an active graphic disposed on the article's bodyside liner and/or outer cover, and the active graphic consists essentially of insoluble ink. In particular embodiments, the article includes an active graphic disposed on the article's bodyside liner and/or outer cover, and the article is adapted to provide for an at least partial disappearance of the active graphic without requiring that the active graphic directly contact liquid to effect the at least partial disappearance.

20 Claims, 8 Drawing Sheets

U.S. PATENT DOCUMENTS

| | | | |
|---|---|---|---|
| 6,635,797 B2 * | 10/2003 | Olson et al. | 604/361 |
| 6,645,190 B1 | 11/2003 | Olson et al. | |
| 6,710,221 B1 * | 3/2004 | Pierce et al. | 604/361 |
| 6,761,711 B1 | 7/2004 | Fletcher et al. | |
| 2001/0053898 A1 * | 12/2001 | Olson et al. | 604/361 |
| 2002/0010454 A1 | 1/2002 | Van Gompel et al. | |
| 2003/0125682 A1 | 7/2003 | Olson et al. | |
| 2003/0139713 A1 | 7/2003 | Olson et al. | |
| 2004/0064113 A1 | 4/2004 | Erdman | |
| 2004/0064115 A1 | 4/2004 | Arora et al. | |
| 2004/0138633 A1 | 7/2004 | Mishima et al. | |
| 2004/0254549 A1 | 12/2004 | Olson et al. | |
| 2005/0085784 A1 | 4/2005 | Leminh et al. | |
| 2005/0096623 A1 | 5/2005 | Nhan et al. | |
| 2005/0124962 A1 | 6/2005 | Wyngaard | |
| 2005/0137085 A1 | 6/2005 | Zhang et al. | |
| 2005/0148961 A1 | 7/2005 | Sosalla et al. | |
| 2005/0256488 A1 | 11/2005 | Sperl | |
| 2006/0004333 A1 | 1/2006 | Olson | |
| 2006/0004336 A1 | 1/2006 | Zhang et al. | |
| 2006/0069365 A1 | 3/2006 | Sperl et al. | |

FOREIGN PATENT DOCUMENTS

| | | |
|---|---|---|
| EP | 1 091 716 B1 | 8/2003 |
| GB | 1 245 691 A | 9/1971 |
| WO | WO 99/33426 A1 | 7/1999 |

* cited by examiner

DISPOSABLE ABSORBENT ARTICLE HAVING INTERACTIVE GRAPHICS

BACKGROUND OF THE INVENTION

Disposable absorbent articles are common in today's society. For example, disposable diapers, disposable training pants, and disposable incontinence products are widespread in the marketplace.

In certain applications, it is desirable to alert either the wearer or a caregiver that a garment has been wet. For example, it has been found beneficial to the toilet training process to alert children to the fact that they have had an accident. In other instances, it is desirable to notify a caregiver that wetting has occurred so that the wet garment can be removed, such as with a toilet-training child or with an incontinent person. Various mechanisms can be found in the prior art to provide the wearer and/or caregiver with such notification, but many are unsatisfactory. For example, audible wetness alarms are generally expensive and cumbersome. Water-soluble ink-printed graphics are often expensive, difficult to process, and prone to transfer to a wearer's skin, and generally must be placed in the crotch area of the diaper to ensure that they are wetted, making such graphics difficult to see by both the wearer and the caregiver.

Thus, prior art disposable absorbent garment wetness indicators have been deficient in various regards.

SUMMARY OF THE INVENTION

In response to the aforementioned unmet needs in the art, a new disposable absorbent article has been invented.

In one embodiment, the invention relates to a disposable absorbent article defining a front waist end, a back waist end, and a length which extends between the front and back waist ends. The disposable absorbent article comprises a chassis comprising a bodyside liner, an outer cover, and an absorbent core sandwiched between the liner and the outer cover. The disposable absorbent article further includes an active graphic disposed on at least one of the bodyside liner and the outer cover, the active graphic positioned within one of a frontmost 30% and a backmost 30% of the article's length.

In another embodiment, the invention relates to a disposable absorbent article defining a front waist end, a back waist end, and a length which extends between the front and back waist ends. The disposable absorbent article comprises a chassis comprising a bodyside liner, an outer cover, and an absorbent core sandwiched between the liner and the outer cover. The disposable absorbent article further includes an active graphic disposed on at least one of the bodyside liner and the outer cover, the active graphic consisting essentially of insoluble ink.

In yet another embodiment, the invention relates to a disposable absorbent article comprising a chassis comprising a bodyside liner, an outer cover, and an absorbent core sandwiched between the liner and the outer cover. The disposable absorbent article further includes an active graphic disposed on at least one of the liner and the outer cover, the absorbent article adapted to provide for an at least partial disappearance of the active graphic without requiring that the active graphic directly contact liquid to effect the at least partial disappearance.

The above-mentioned and other features and advantages of the present invention and the manner of attaining them will become more apparent, and the invention itself will be better understood by reference to the drawings and the following description of the drawings.

DETAILED DESCRIPTION OF PARTICULAR EMBODIMENTS

Figure 1:
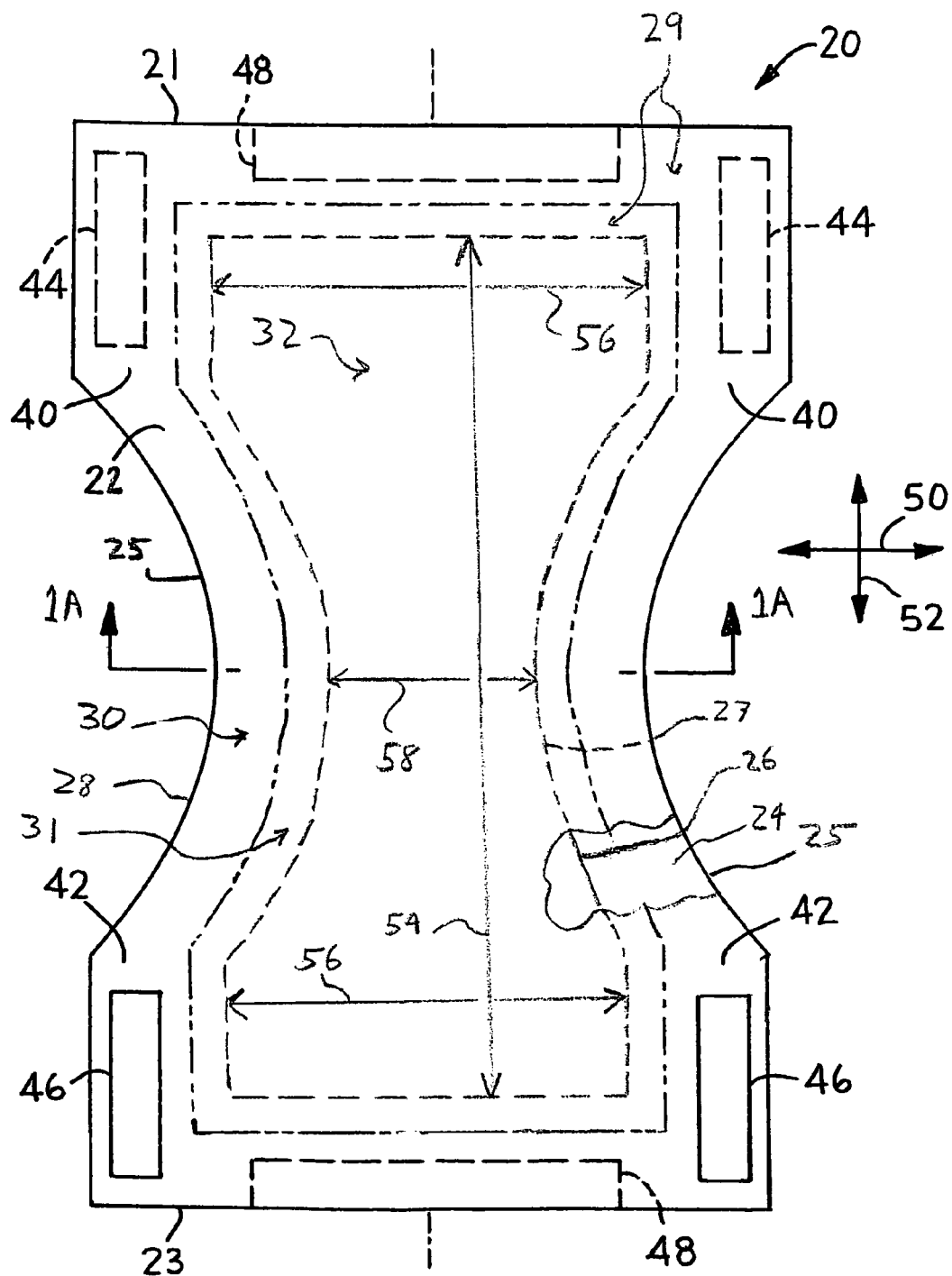
FIG. 1 representatively illustrates a plan view of an absorbent article according to one embodiment of the invention, with portions cut away to show underlying features.
Figure 1A:
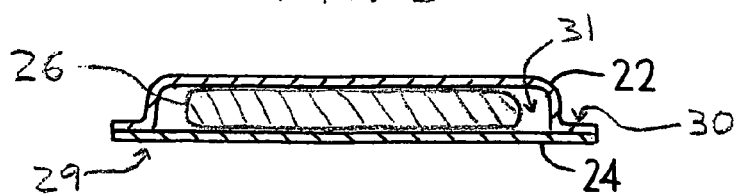
FIG. 1A is a cross-sectional view of the article of FIG. 1 taken at the lines indicated.

As used herein, the following words have the following meanings:

"Connected" refers to the joining, adhering, bonding, attaching, or the like, of two elements. Two elements will be considered to be connected together when they are connected directly to one another or indirectly to one another, such as when each is directly connected to intermediate elements.

"Disposed," "disposed on," "disposed with," "disposed at," "disposed near" and variations thereof are intended to mean that one element can be integral with another element, or that one element can be a separate structure bonded to or placed with or placed near another element.

"Elastic," "elasticized" and "elasticity" mean that property of a material by virtue of which it tends to recover its original size and shape after removal of a force causing a deformation.

"Fiber" or "fibrous" is used to refer to a particulate material wherein the length to diameter ratio of such particulate material is greater than about 10. Conversely, a "nonfiber" or "nonfibrous" material is meant to refer to a particular material wherein the length to diameter ratio of such particle material is about 10 or less.

"Integral" is used to refer to various portions of a single unitary element rather than separate structures bonded to or placed with or placed near one another.

"Inward" and "outward" refer to positions relative to the center of an absorbent garment, and particularly transversely and/or longitudinally closer to or away from the longitudinal and transverse center of the absorbent garment.

"Layer" when used in the singular can have the dual meaning of a single element or a plurality of elements.

"Liquid" means a substance and/or material that flows and can assume the interior shape of a container into which it is poured or placed.

"Liquid impermeable" when used to describe a layer or laminate means that liquid such as urine will not pass through the layer or laminate under ordinary use conditions in a direction generally perpendicular to the plane of the layer or laminate at the point of liquid contact.

"Permanently bonded" refers to the joining, adhering, connecting, attaching, or the like, of two elements of an absorbent garment such that the elements tend to be and remain bonded during normal use conditions of the absorbent garment.

"Releasably attached," "releasably bonded," "releasably engaged" and variations thereof refer to two elements being connected or connectable such that the elements tend to remain connected absent a separation force applied to one or both of the elements, and the elements being capable of separation without substantial permanent deformation or rupture. The required separation force is typically beyond that encountered while wearing the absorbent garment.

"Tension" includes a uniaxial force tending to cause the extension of a body or the balancing force within that body resisting the extension.

Various aspects of the invention shall now be described in the context of a child's training pant, although it is understood that the principles of the invention have applicability to any variety of disposable absorbent articles, such as, for example, diapers, incontinence products, feminine hygiene products, disposable swimwear, and the like. As used herein, the phrase "absorbent article" refers to devices that absorb and contain body fluids, and more specifically, refers to devices that are placed against or near the skin to absorb and contain urine discharged from the body. The term "disposable" is used herein to describe absorbent articles that are not intended to be laundered or otherwise restored or reused as an absorbent article after being soiled.

Disposable absorbent articles according to various embodiments of the invention are representatively illustrated in FIG. 1-9 in the form of a child's training pant 20 in a laid-flat configuration. The pant 20 includes a fluid pervious bodyside liner 22, a liquid impervious garment-side outer cover 24 joined to the liner 22, and an absorbent core 26 positioned between the liner 22 and the outer cover 24. Together, the liner 22, outer cover 24, and absorbent core 26 define an absorbent article chassis 28. Disposable absorbent articles and components thereof, including the liner, outer cover, absorbent core and any individual layers of these components, generally have a body-facing surface and a garment-facing surface. As used herein, "body-facing surface" refers to that surface of the article or component which is intended to be worn toward or placed adjacent to the body of the wearer, while the "garment-facing surface" is on the opposite side and is intended to be worn toward or placed adjacent to the wearer's garments when the disposable absorbent article is worn. The garment 20 defines a front end 21, a back end 23, and a length which extends between the front end 21 and the back end 23.

In particular embodiments, the liquid impermeable outer cover 24 can be both liquid and vapor impermeable, or can be liquid impermeable and vapor permeable. The liquid impermeable outer cover 24 is desirably manufactured at least in part from a thin plastic film, although other flexible liquid impermeable materials can also be used. The liquid impermeable outer cover prevents waste material from wetting articles, such as bedsheets and clothing, as well as the wearer and caregiver. The liquid impermeable outer cover 24 can include other materials, such as cloth-like nonwoven materials well known in the art.

The liner 22 is desirably compliant, soft feeling, and non-irritating to the child's skin. Further, the liner 22 can be less hydrophilic than the absorbent core, to present a relatively dry surface to the wearer and permit liquid to readily penetrate through its thickness. Alternatively, the liner can be more hydrophilic or can have essentially the same affinity for moisture as the absorbent core to present a relatively wet surface to the wearer to increase the sensation of being wet. This wet sensation can be useful as a training aid.

As discussed above, the absorbent core 26 may be located between the outer cover 24 and the liner 22. The absorbent core 26 can be any structure which is generally compressible, conformable, non-irritating to the child's skin, and capable of absorbing and retaining liquids and certain body wastes, and may be manufactured in a wide variety of sizes and shapes, such as, for example, hourglass shaped (FIG. 1) or rectangular shaped (FIG. 2). The absorbent core 26 may be manufactured from a wide variety of liquid absorbent materials commonly used in the art, such as cellulosic wood pulp fluff. The absorbent core 26 of the illustrated embodiments further includes superabsorbent polymer, as described in more detail below. Also, in certain embodiments, the absorbent core 26 of the present invention includes a binder material, such as an elastomeric binder material. Examples of elastomeric binders suitable for use in conjunction with the present invention are described in the Examples below. Moreover, the absorbent core 26 of particular embodiments of the present invention can but need not exhibit unique planar expansion characteristics, as shall be more fully explained below.

The absorbent article 20 can also incorporate other materials or components designed primarily to receive, temporarily store, and/or transport liquid to different regions of the absorbent core, thereby maximizing the absorbent capacity of the absorbent core. One suitable additional component is commonly referred to as a surge layer (not shown) and comprises a material having a basis weight of about 20 to about 200 grams per square meter, and in particular embodiments comprises a through-air-bonded-carded web of a homogenous blend of 60 percent 3 denier type T-256 bicomponent fiber comprising a polyester core/polyethylene sheath and 40 percent 6 denier type T-295 polyester fiber, both commercially available from Kosa Corporation of Salisbury, N.C., U.S.A.

Absorbent articles in accordance with the present invention can have front side panels 40 and back side panels 42 disposed on each side of the absorbent core 26. The side panels 40 and 42 can be permanently attached along seams to one or more components in the central section of the article, such as the liner and/or outer cover, using attachment means known to those skilled in the art such as adhesive, thermal or ultrasonic bonding. Alternatively, the side panels can be formed as an integral portion of one or more components of the article 20, such as a generally wider portion of the outer cover and/or liner, as is representatively illustrated in FIGS. 1-8.

In particular embodiments, such as a child's training pant, the front side panels 40 are attached to the back side panels 42 to define a three-dimensional pant-like configuration (not shown). In such embodiments, the front and back side panels can be permanently bonded together using bonding means known in the art, or can be releasably connected with one another such as by a fastening system. A refastenable pant can comprise front fastening components 44 and mating fastening components 46. The side panels 40 and 42 suitably, although not necessarily, comprise an elastic material.

Any of the materials or components mentioned above can be non-stretchable, stretchable, or elastomeric. The absorbent articles of the present invention can also include waist elastics 48, leg elastics (not shown), and/or containment flaps (not shown), all of which are well known in the art.

Examples of the various materials and components that are referenced above and that are suitable for use in conjunction with the present invention are disclosed in U.S. Pat. No. 6,645,190 issued to C. P. Olson et al., U.S. Pat. No. 6,761,711 issued to Fletcher et al., U.S. patent application Ser. No. 10/729,485 in the name of Wyngaard, U.S. patent application Ser. No. 10/690,424 in the name of LeMinh et al., and U.S. patent application Ser. No. 10/835,638 in the name of Sperl, the entireties of which are hereby incorporated by reference to the extent consistent herewith.

Methods of absorbent article assembly per se are well known in the art, and a detailed recitation of the specific technical aspects of such methods is not necessary for an understanding of the present invention. Processes suitable for the assembly of disposable training pants are disclosed in U.S. Pat. Nos. 6,652,167 and 6,514,187 issued to Coenen et al., each of which is hereby incorporated by reference to the extent consistent herewith.

As used herein, "superabsorbent polymer," "superabsorbent material," "superabsorbent materials" and the like are intended to refer to a water-swellable, water-insoluble organic or inorganic material capable, under the most favorable conditions, of absorbing at least about 10 times its weight and, desirably, at least about 15 times its weight in an aqueous solution containing 0.9 weight percent of sodium chloride. Such materials include, but are not limited to, hydrogel-forming polymers that are alkali metal salts of: poly(acrylic acid); poly(methacrylic acid); copolymers of acrylic and methacrylic acid with acrylamide, vinyl alcohol, acrylic esters, vinyl pyrrolidone, vinyl sulfonic acids, vinyl acetate, vinyl morpholinone and vinyl ethers; hydrolyzed acrylonitrile grafted starch; acrylic acid grafted starch; maleic anhydride copolymers with ethylene, isobutylene, styrene, and vinyl ethers; polysaccharides such as carboxymethyl starch, carboxymethyl cellulose, methyl cellulose, and hydroxypropyl cellulose; poly(acrylamides); poly(vinyl pyrrolidone); poly(vinyl morpholinone); poly(vinyl pyridine); and copolymers and mixtures of any of the above and the like. The hydrogel-forming polymers are suitably lightly cross-linked to render them substantially water-insoluble. Cross-linking may be achieved by irradiation or by covalent, ionic, van der Waals, or hydrogen bonding interactions, for example. A suitable superabsorbent material is a lightly cross-linked hydrocolloid. Specifically, a more suitable superabsorbent material is a partially neutralized polyacrylate salt. Superabsorbent materials useful in the present invention are generally available from various commercial vendors, such as, for example, the Dow Chemical Company, Midland, Mich., U.S.A., Stockhausen Inc., Greensboro, N.C., or the BASF Corporation, Portsmouth, Va., U.S.A.

Suitably, the superabsorbent material is in the form of particles which, in the unswollen state, have maximum diameters ranging between about 50 and about 1,000 microns; suitably, between about 100 and about 800 microns; more suitably, between about 200 and about 650 microns; and most suitably, between about 300 and about 600 microns, as determined by sieve analysis according to American Society for Testing Materials Test Method D-1921. It is understood that the particles of superabsorbent material may include solid particles, porous particles, or may be agglomerated particles including many smaller particles agglomerated into particles falling within the described size ranges.

The disposable absorbent article of the present invention includes an active graphic disposed thereon. The term "active graphic" as used herein refers to an appearing graphic, a disappearing graphic, or a combination of appearing and disappearing graphics. The term "appearing graphic" is used herein to refer to a graphic that becomes visible or becomes significantly more visible after the article has been wetted. Conversely, the term "disappearing graphic" is used herein to refer to a graphic that becomes invisible or significantly less visible after the article has been wetted. A graphic is considered an "active graphic" as used herein if the graphic is observed to appear, partially appear, disappear, partially disappear, or become obscured when an absorbent article having graphics is tested in accordance with the Active Graphic Test outlined below. In the context of the toilet training process, the changed condition of the graphic presents a tool for a caregiver to interact with the toilet-training child and explain why the graphic changed. This is particularly useful at the stage of toilet training where a child is being taught to be aware of going potty and the need to use the bathroom. Active graphics are believed to make children more interested in the toilet training process and therefore lead to enhanced results.

In particular embodiments, the active graphic is disposed on at least one of the bodyside liner and the outer cover. The active graphic can be disposed on either surface of any layer with either the bodyside liner or the outer cover, or disposed on a separate piece of material that is connected to either the bodyside liner or the outer cover, so long as the active graphic is visible from some vantage point when the product is in either an initial dry state (such as in the case of a disappearing graphic) or a wetted state (such as in the case of an appearing graphic). Thus, unless specified otherwise, the phrase "active graphic" is used herein to convey that a graphic or graphic portion either appears or disappears to a person viewing the absorbent article from at least one vantage point. For example, active graphics can be positioned within an article such that they disappear or appear when the product is wetted only to one viewing the graphic from the body-facing surface of the article. Alternatively, active graphics can be positioned within an article such that they disappear or appear when the product is wetted only to one viewing the graphic from the garment-facing surface of the article. In another alternative, the active graphic could disappear or appear when the product is wetted simultaneously both to a person viewing the graphic from the body-facing surface of the article as well as to a person viewing the graphic from the garment-facing surface of the article.

It has been discovered that, in particular embodiments, it can be advantageous to position active graphics near the front and/or back waist ends of disposable absorbent articles. For example, as representatively illustrated in FIGS. 3 and 4, positioning the active graphic 60 near the front waist end 21 of the training pant 20 allows a child to look down when he or she is wearing the product and easily view the graphic. This advantage can hold true whether the graphic is visible from the body-facing surface or the garment-facing surface of the product. For instance, in an embodiment in which an active graphic is placed near the front waist end 21 and is visible from the body-facing surface (i.e., when viewed through the liner), the wearer can pull open the waistband of the pant to look inside to see if the active graphic has changed condition. In another example (not shown), an active graphic can be placed near the back waist end 23, so that a caregiver can inspect the status of the article. In particular embodiments, the active graphic is positioned within a frontmost 30%, more particularly a frontmost 25%, more particularly a frontmost 20%, and still more particularly a frontmost 15% of the article's length. In particular embodiments, the active graphic is positioned within a backmost 30%, more particularly a backmost 25%, more particularly a backmost 20%, and still more particularly a backmost 15% of the article's length. "Frontmost" and "backmost" refer to the area of the article longitudinally closest to the article's front waist end 21 and back waist end 23, respectively.

In particular embodiments, the active graphic 60 consists essentially of insoluble ink. "Consists essentially of insoluble ink" means that the active graphic is substantially devoid of soluble inks, but the phrase "consists essentially of insoluble ink" does not disallow the presence of other, non-essential components such as fillers, brighteners, overlaquers, film coatings, and the like. The active graphic 60 in accordance with particular embodiments of the present invention can appear and/or disappear without the use of soluble inks, avoiding the aforementioned problems which exist with certain prior art approaches. In particular embodiments, the active graphic consists essentially of substantially inert inks. "Substantially inert inks" means inks that do not experience physical changes to their condition (e.g., fading, dissolving, and the like) in response to such ambient environmental conditions as temperature, humidity, oxygen, sunlight, and the like during the expected useful life of a product (e.g., within 24 hours of removal from product packaging).

In particular embodiments, the disposable absorbent article of the present invention is adapted to provide for an at least partial appearance and/or disappearance of the active graphic 60 without requiring that the active graphic directly contact liquid to effect the disappearance. In particular embodiments, this aspect of the invention can avoid the need to use liquid-soluble inks, and can avoid the need to place the active graphic 60 only in those regions of the product having a high probability of being exposed to liquid (such as the crotch region).

Particular but merely representative embodiments of the invention shall now be described with particular reference to FIGS. 3-7. In the illustrated embodiments, the outer cover 24 has in particular embodiments a graphic 60 disposed thereon. The graphic 60 is visible from the body-facing side of the pant 20. For example, in a preferred embodiment in which the graphic 60 is under the liner 22, the graphic 60 should be visible through the liner 22 at least when the product is in an initial dry state (as in the embodiments illustrated in FIGS. 3 and 5). The graphic 60 can be printed or otherwise disposed directly on either the body-facing surface or garment-facing surface of any layer of the outer cover 24. Alternatively, the graphic 60 can be printed or otherwise disposed on a piece of material separate from the outer cover 24 which is affixed to one or more layers of the outer cover 24.

Figure 2:
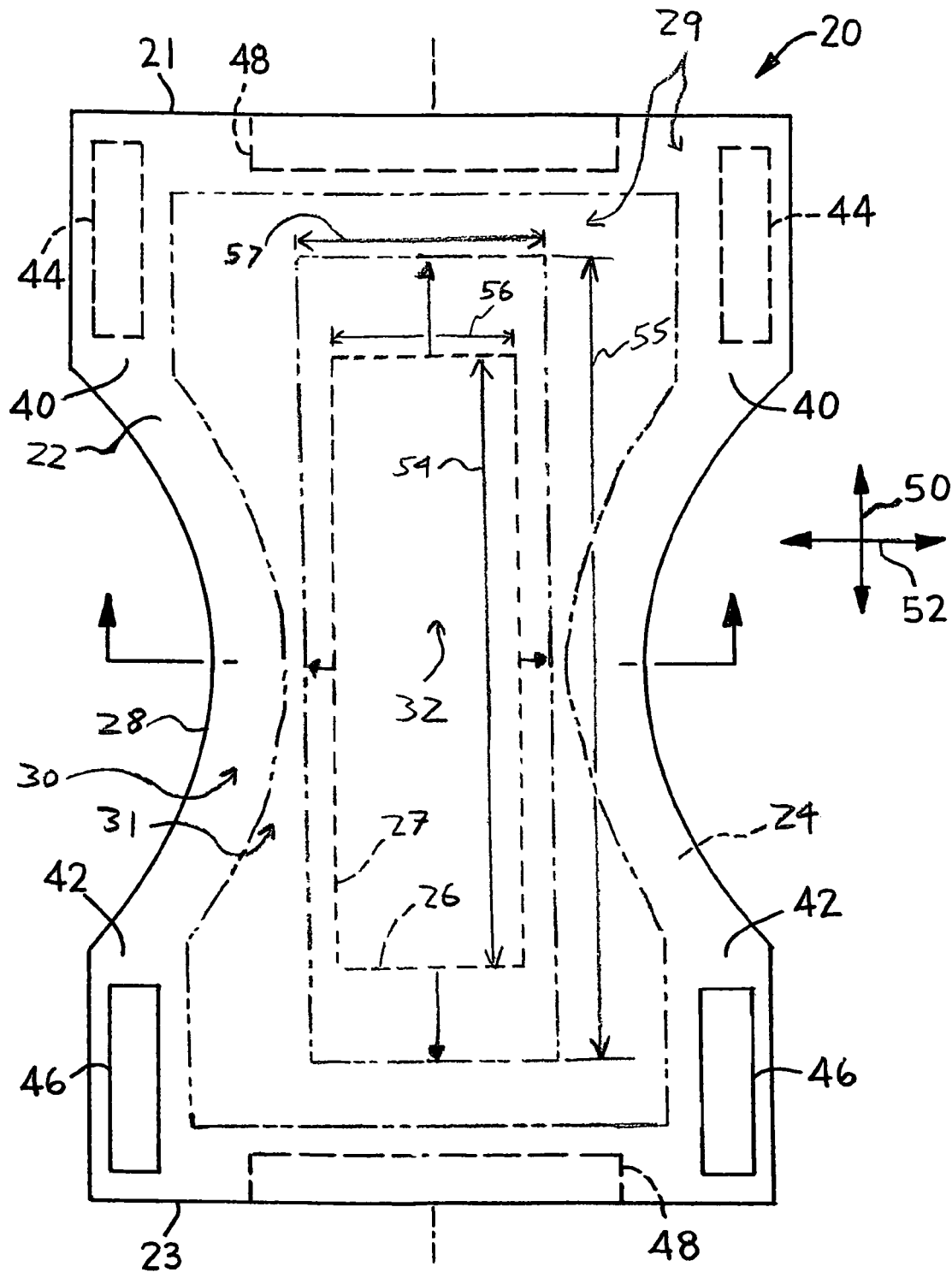
FIG. 2 representatively illustrates a plan view of an absorbent article according to another embodiment of the invention.
Figure 3:
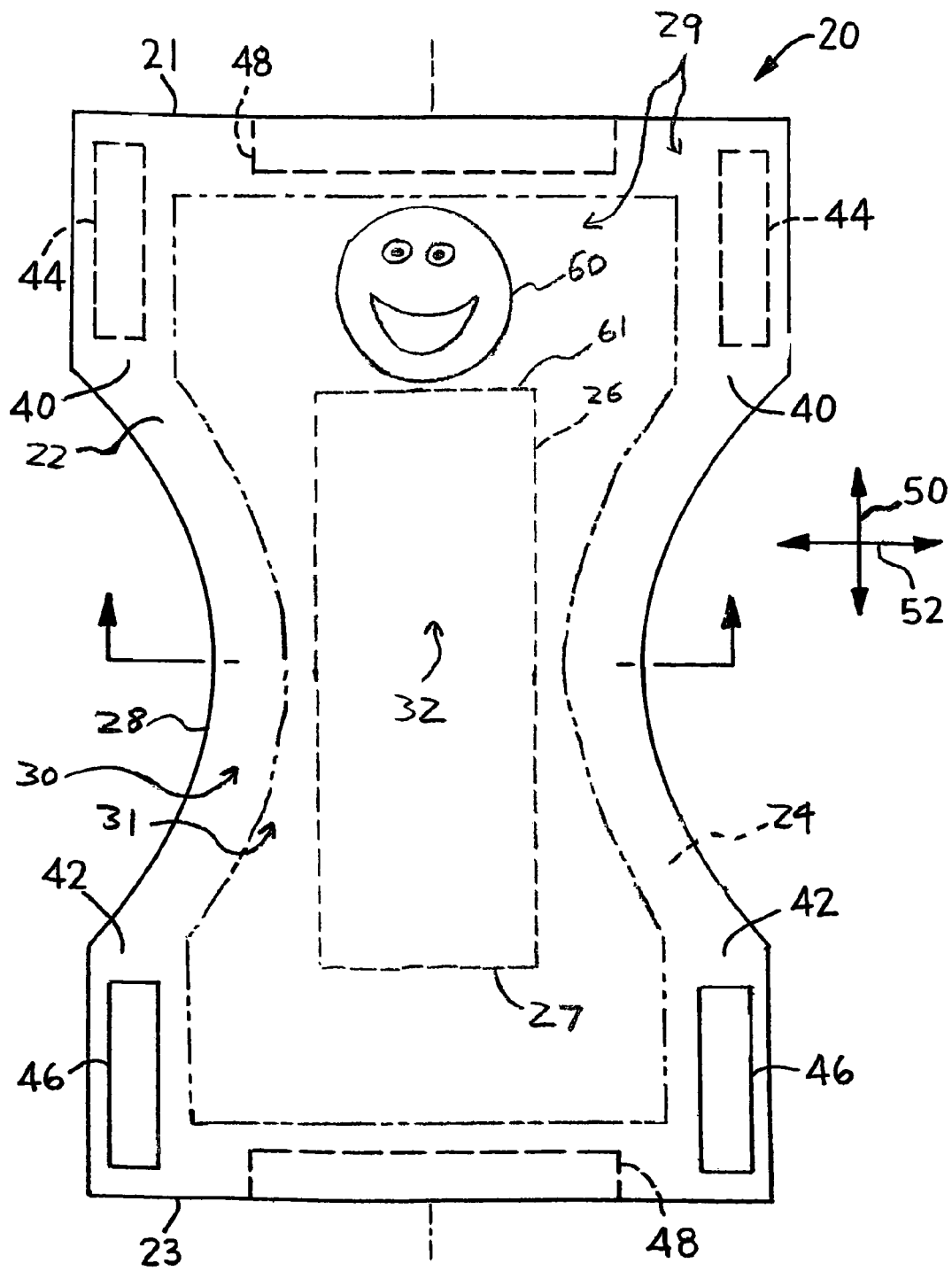
FIG. 3 representatively illustrates a plan view of an absorbent article prior to exposure to liquid according to yet another embodiment of the invention.

As representatively illustrated in FIGS. 1-3, the absorbent core defines an absorbent core perimeter 27. The liner 22 and outer cover 24 are superposed on opposite surfaces of the absorbent core 26, and extend beyond the absorbent core perimeter 27 to define a chassis peripheral area 29. In particular embodiments, the liner 22 and outer cover 24 are connected to each other within at least a portion of the chassis peripheral area 29 to define a sealed area 30. The sealed area 30 can prevent components of the absorbent core 26, such as superabsorbent material and pulp fibers, from escaping. Moreover, in particular embodiments as shall be explained below, the sealed area 30 can constrict the planar growth of the absorbent core 26.

The absorbent core 26 of the present invention can exhibit planar growth when exposed to fluid. "Planar growth" as used herein refers to a lengthening (in the longitudinal direction 50) or a widening (in the transverse direction 52) of the absorbent core 26 when wetted, or both, as opposed to a thickening. For example, as representatively illustrated in FIG. 2, the absorbent core 26 can expand in the longitudinal direction 50 from a dry length 54 to a wet length 55. Alternatively or additionally, the absorbent core 26 can expand in the transverse direction 52 from a dry width 56 to a wet width 57. In particular embodiments, the planar growth can be quantified using the In-Product Planar Growth Test or the Modified In-Product Planar Growth Test, both described below.

In particular embodiments, the absorbent core 26 can expand at least about 5%, more particularly at least about 10%, more particularly at least about 15%, more particularly at least about 20%, more particularly at least about 25%, more particularly at least about 30%, more particularly at least about 35%, more particularly at least about 40%, more particularly at least about 45%, and still more particularly at least about 50% in the longitudinal direction 50. Furthermore, in particular embodiments, the absorbent core 26 can expand at least about 5%, more particularly at least about 10%, more particularly at least about 15%, more particularly at least about 20%, more particularly at least about 25%, more particularly at least about 30%, more particularly at least about 35%, more particularly at least about 40%, more particularly at least about 45%, and still more particularly at least about 50% in the transverse direction 52. For example, in the embodiment illustrated in FIG. 2, the absorbent core 26 is shown as having expanded approximately 30% in the longitudinal direction 50 and approximately 25% in the transverse direction 52.

In particular embodiments, the bodyside liner 22 and the outer cover 24 are substantially unconnected to each other within a portion of the chassis peripheral area 29 to define an open area 31. The open area 31 can accommodate the planar growth of the absorbent core 26. Such a design can be desirable for a number of reasons. For example, to improve the fit and/or donning attributes of various absorbent articles, it can be desirable to design absorbent articles with stretchable or elastomeric components, such as the liner 22, outer cover 24, side panels 40/42, or to provide elasticity to the product via such means as waist elastics 48 or leg elastics (not shown). Placing an absorbent core near or over such stretchable or elastomeric components can hinder the ability of the elastomeric components to enhance product fit or donning as intended. In other words, the ability of the stretchable or elastomeric components to easily stretch can be stymied by the absorbent core, even if the absorbent core possesses some amount of extensibility. The present invention can in certain embodiments provide an absorbent article having an absorbent core that is relatively small in length and/or width in its initial dry state, and that will not assume an expanded length and/or width until it begins to soak up fluid. In this way, the fit and donning functions of the stretchable/elastomeric garment are maximized initially, and only impacted, if at all, near the end of the useful life of the product (i.e., after is has been partially or completely wet or soiled).

For example, in the embodiment of FIG. 2, the absorbent core is initially spaced relatively far from the elastomeric side panels 40/42 and the waist elastic 48, thus rendering those components free to perform their intended function during donning and during wear until the absorbent core 26 has undergone significant expansion. Further, if portions of the liner 22 or outer cover 24 within the chassis peripheral area 29 are stretchable or elastomeric, those areas are initially free to stretch and provide the intended product benefit.

The absorbent core 26 defines an absorbent core area 32, which is the area within the absorbent core perimeter 27 in its initial dry state. In particular embodiments, the absorbent article according to the present invention can include an open area 31 that is at least about 5%, more particularly at least about 10%, more particularly at least about 15%, more particularly at least about 20%, more particularly at least about 25%, more particularly at least about 30%, more particularly at least about 35%, more particularly at least about 40%, still more particularly at least about 50%, still more particularly at least about 60%, and still more particularly at least about 75% that of the absorbent core area 32. In particular embodiments, the more the absorbent core 26 is expected to expand upon wetting, the larger should be the open area relative to the size of the absorbent core area 26. "Area" as used herein when referring to a portion of a product refers to the particular area in question as measured when the product is in a laid-flat condition, uncontracted by any elastic components within the article.

Figure 4:
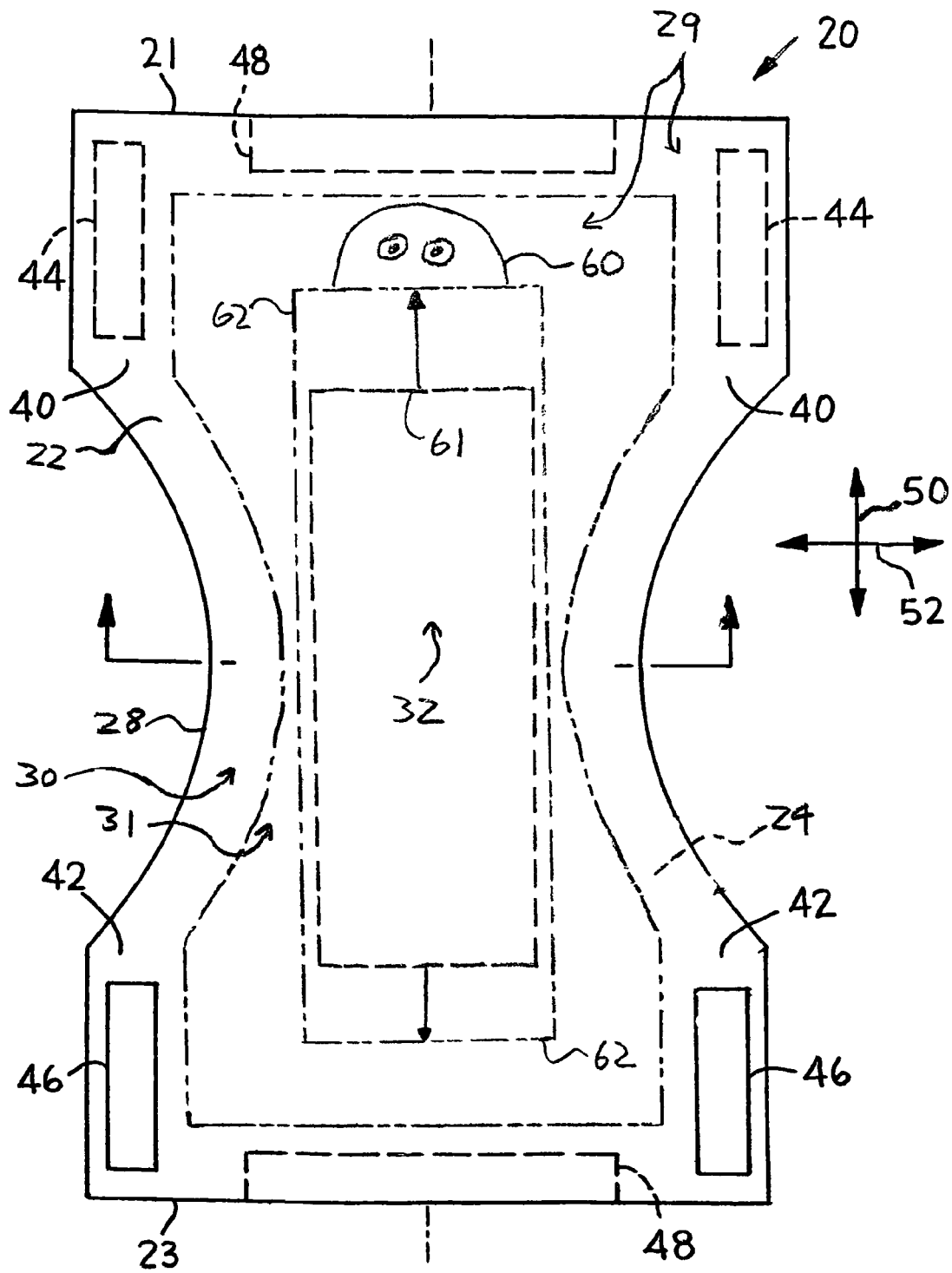
FIG. 4 representatively illustrates the article of FIG. 3 following exposure to liquid.

In particular embodiments, the active graphic is desirably positioned such that when the absorbent core 26 experiences planar growth, at least a portion of the active graphic 60 becomes concealed. For example, as representatively illustrated in FIGS. 3 and 4, the graphic 60 is fully visible when viewed from the body-facing side of the article 20 when the absorbent core 26 is in an initial dry state 61. However, the graphic 60 becomes at least partially concealed by the absorbent core 26 after it has expanded to an expanded state 62, such as a fully saturated state according to the In-Product Planar Growth Test described below. In the embodiment of FIG. 4, the planar growth of the absorbent core 26 in the longitudinal direction 50 has concealed the lower half of the active graphic 60.

Figure 5:
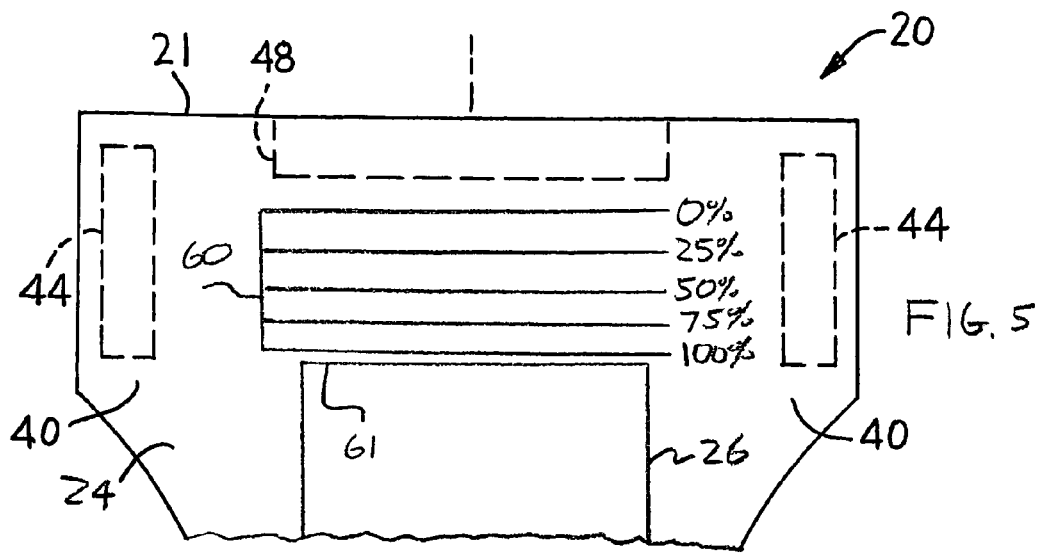
FIG. 5 representatively illustrates a plan view of a portion of an absorbent article according to still another embodiment of the invention.
Figure 6:
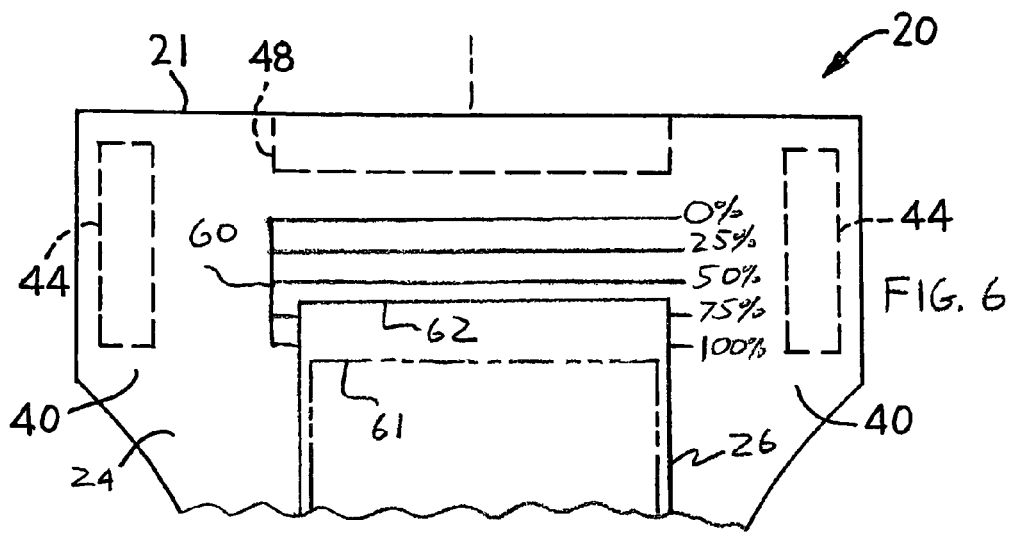
FIG. 6 representatively illustrates the absorbent article portion of FIG. 5 following exposure to liquid.
Figure 7:
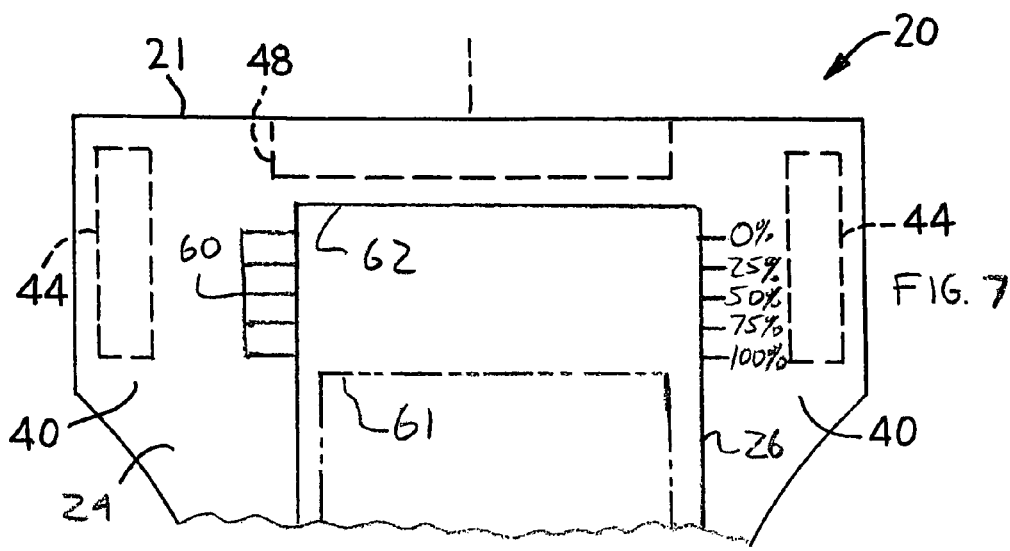
FIG. 7 representatively illustrates the absorbent article portion of FIG. 5 following exposure to additional liquid.
Figure 8:
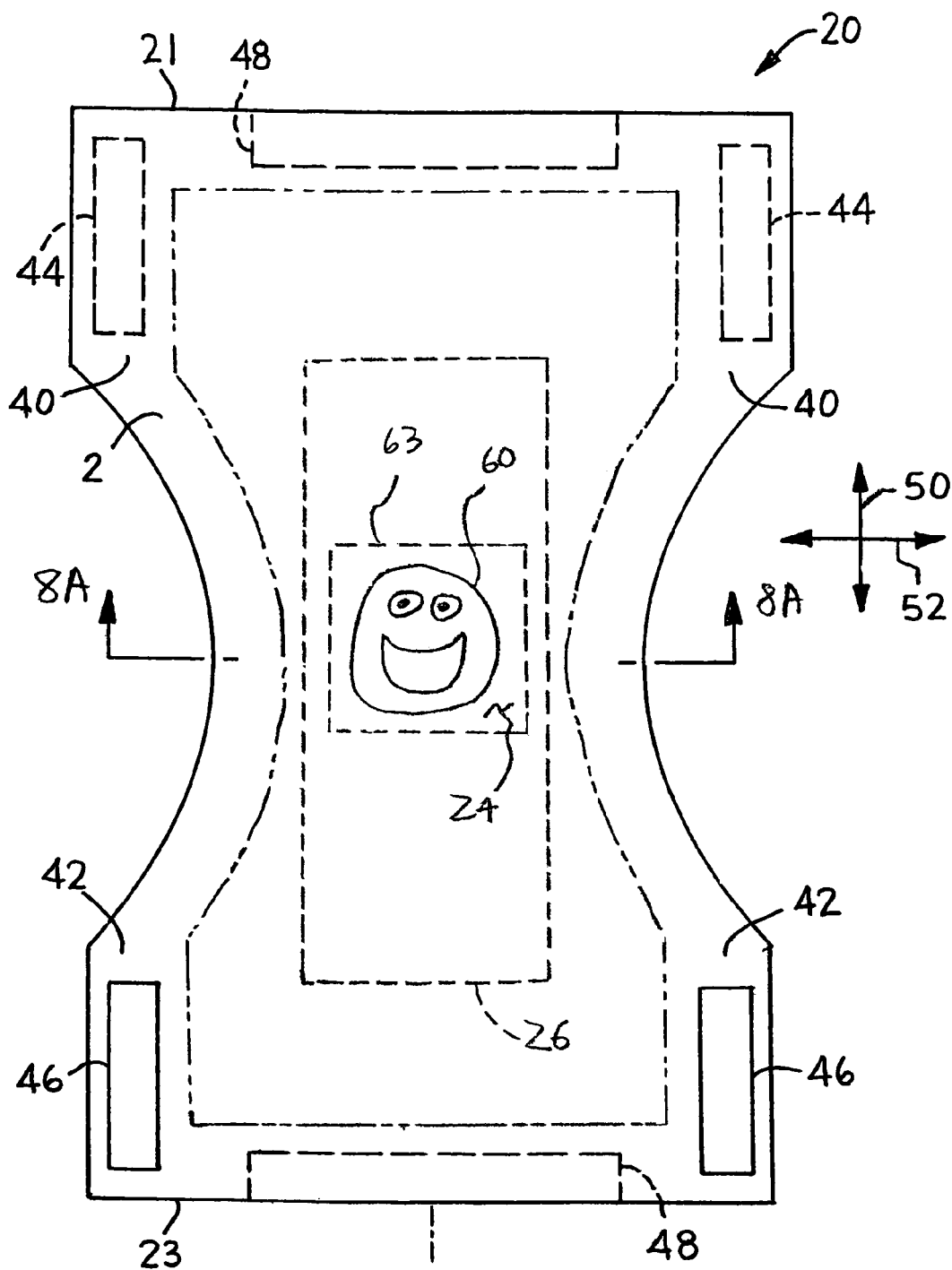
FIG. 8 representatively illustrates a plan view of an absorbent article according to yet another embodiment of the invention.
Figure 8A:
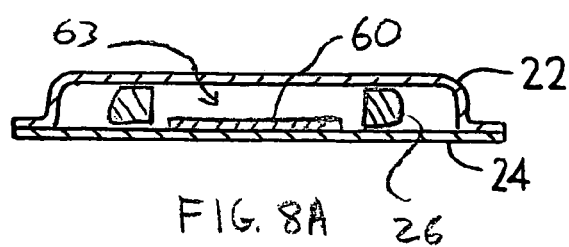
FIG. 8A is a cross-sectional view of the article of FIG. 8 taken at the lines indicated.

In a particular embodiment, the graphic can depict an absorption capacity "meter," as representatively illustrated in FIGS. 5-7. When the absorbent core 26 is in an initial dry state 61, the "meter" indicates that 100% of the core's absorption capacity remains available to receive fluid insults. As the absorbent core begins to absorb fluid, expand, and advance along the graphic 60, the "meter" accordingly indicates a decreasing percentage amount of available absorption capacity.

The graphic 60 can in particular embodiments be placed anywhere in the product as long as it becomes either appears or disappears following some amount of planar growth by the absorbent core 26. For example, as described above, the graphic 60 can be disposed on a layer of the outer cover 26 such that it will be concealed upon planar growth of the absorbent core 26 when viewed from the body-facing side of the garment 20. Alternatively, the graphic 60 can be disposed on the liner 22 such that it will be concealed upon planer growth of the absorbent core 26 when viewed from the garment-facing surface of the garment 20, such as when viewed through a transparent or translucent portion of the outer cover 24. In yet another alternative, representatively illustrated in FIG. 8, the graphic 60 can be disposed on the outer cover 26 beneath an opening 63 within the absorbent core 26. In such an embodiment, planar growth of the absorbent core 26 can occur toward the longitudinal and/or transverse centerlines of the product ("filling" the opening as it expands), thereby at least partially overlapping and concealing the graphic 60. In still another embodiment, the planar growth of the absorbent core 26 can shift the position of the opening such that it conceals the graphic 60 (i.e., a disappearing graphic) and/or reveals a new graphic (i.e., an appearing graphic).

In other embodiments, it is desirable that the absorbent article 20 include little or no open area 31 within the chassis peripheral area 29. The dearth of open area 31 can restrict the planar growth of the absorbent core 26. Such a design can be desirable for a number of reasons. For example, if the chassis peripheral area 29 contains little or no room to accommodate the absorbent core's planar growth, the absorbent core can buckle, bunch up, bulge, or otherwise result in deformation of the absorbent article 20. In particular embodiments, such as in a child's training pant, such deformations can signal to the wearer that he or she has wet the garment due to the discomfort caused by the bulging pant. Furthermore, the deformation can result in a visible change to the appearance of the product, signaling to a caregiver that the garment has been wet and should be changed.

Figure 9A:
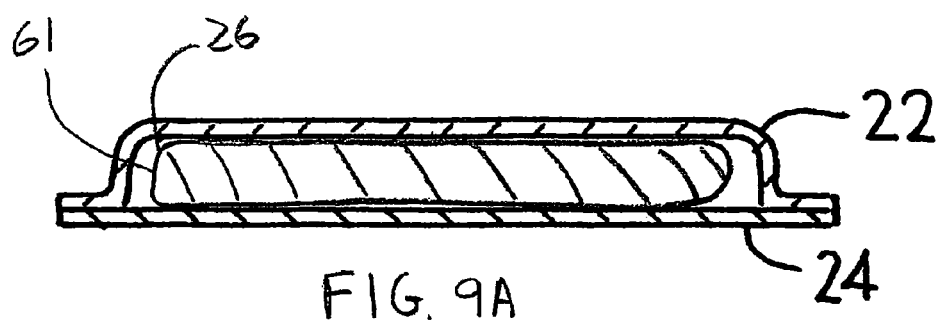
FIG. 9A representatively illustrates a cross-sectional view of an absorbent article prior to exposure to liquid according to an embodiment of the invention similar to the embodiment representatively illustrated in FIGS. 1 and 1A.
Figure 9B:
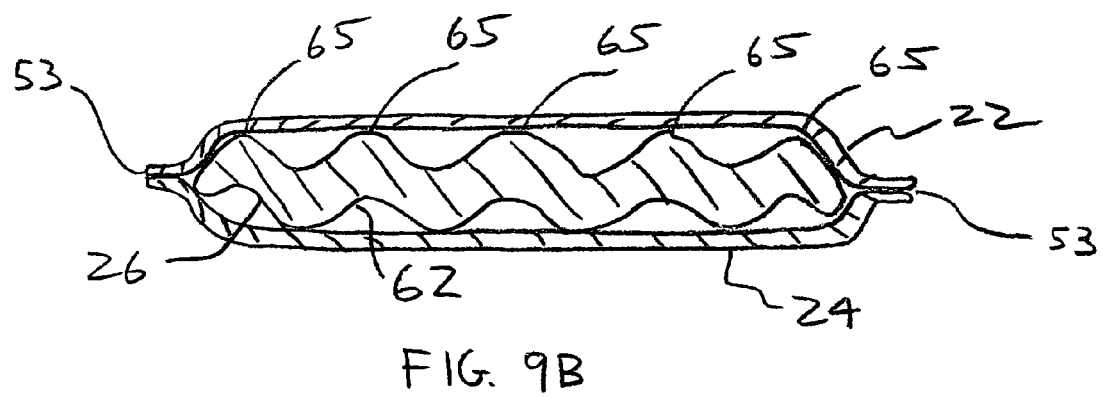
FIG. 9B representatively illustrates the article of FIG. 9A following exposure to liquid.

In particular embodiments, the deformation can provide a leakage-barrier function within the article. For example, as representatively illustrated in FIGS. 9A and 9B, an absorbent core 26 is provided within a chassis 28 having minimal open area 31 when the absorbent core 26 is in an initial dry state 61 (FIG. 9A). However, after the product has been insulted with a sufficient amount of fluid, the absorbent core 26 experiences planar growth (in this case, in the transverse direction 52), and, since there is little room to expand, the absorbent core 26 develops buckles or folds 65. These folds 65 can extend along the length of the absorbent article 20 to function as leakage barrier, helping to prevent bodily waste from migrating toward the lateral sides 25 of the product. In an alternative embodiment (not shown), the planar growth can occur predominantly in the longitudinal direction 50, such that the buckles or folds would extend across the width of the absorbent article 20 to prevent fluid from migrating toward the front and/or back ends 21,23 of the product.

Accordingly, in particular embodiments, the absorbent article according to the present invention can include an open area 31 that is at most about 50%, more particularly at most about 40%, more particularly at most about 30%, more particularly at most about 20%, more particularly at most about 15%, more particularly at most about 10%, more particularly at most about 5%, more particularly at most about 2%, and yet more particularly about 0% that of the absorbent core area 32. In particular embodiments, the more deformation and/or buckling that is desired in the product upon wetting, the smaller should be the open area relative to the amount of anticipated planar growth of the absorbent core 26.

Without wishing the following theory to limit the scope of the invention, it is believed that certain of the presently disclosed embodiments of disposable absorbent articles having absorbent cores according the present invention derive their planar growth characteristics from various unique combinations of superabsorbent material, elastomeric binder material, and other absorbent core materials. However, it is the inventors' intention that the claims set forth the scope of the invention, and that the presence or absence of particular absorbent core components are not intended to define the boundaries of the invention. Examples of constructions of absorbent cores that can provide the requisite planar growth characteristics include those disclosed in U.S. patent application Ser. No. 10/699,193 in the name of Sawyer et al., Ser. No. 10/739,385 in the name of Zhang et al., Ser. No. 10/883,174 in the name of Zhang et al, and Ser. No. 10/955,430 in the name of Sperl et al., all assigned to Kimberly-Clark Worldwide, Inc., the contents of which are hereby incorporated by reference to the extent consistent herewith. A process suitable for constructing particular embodiments of such stretchable absorbent pads is described in U.S. Pat. No. 6,362,389 to McDowall et al. and assigned to Kimberly-Clark Worldwide, Inc., the content of which is hereby incorporated by reference to the extent consistent herewith. Moreover, it is believed that, with respect to one or more of the just-listed exemplary processes (such as the process disclosed in U.S. Pat. No. 6,362,389), the amount of longitudinal and/or transverse planar growth exhibited by absorbent cores can in particular embodiments be increased by the use of relatively high polymer melt temperatures, relatively low polymer throughput rates as compared to the speed of the absorbent core forming conveyor or drum, relatively high pressure of the air used to blow the binder polymer onto the forming surface, and the use of substantially integral, homogenous absorbent core structures (as opposed to absorbent cores comprised of multiple layers).

Particular embodiments according to the present invention shall be described by way of the Examples Which follow below.

In-Product Planar Growth Test

Figure 10:
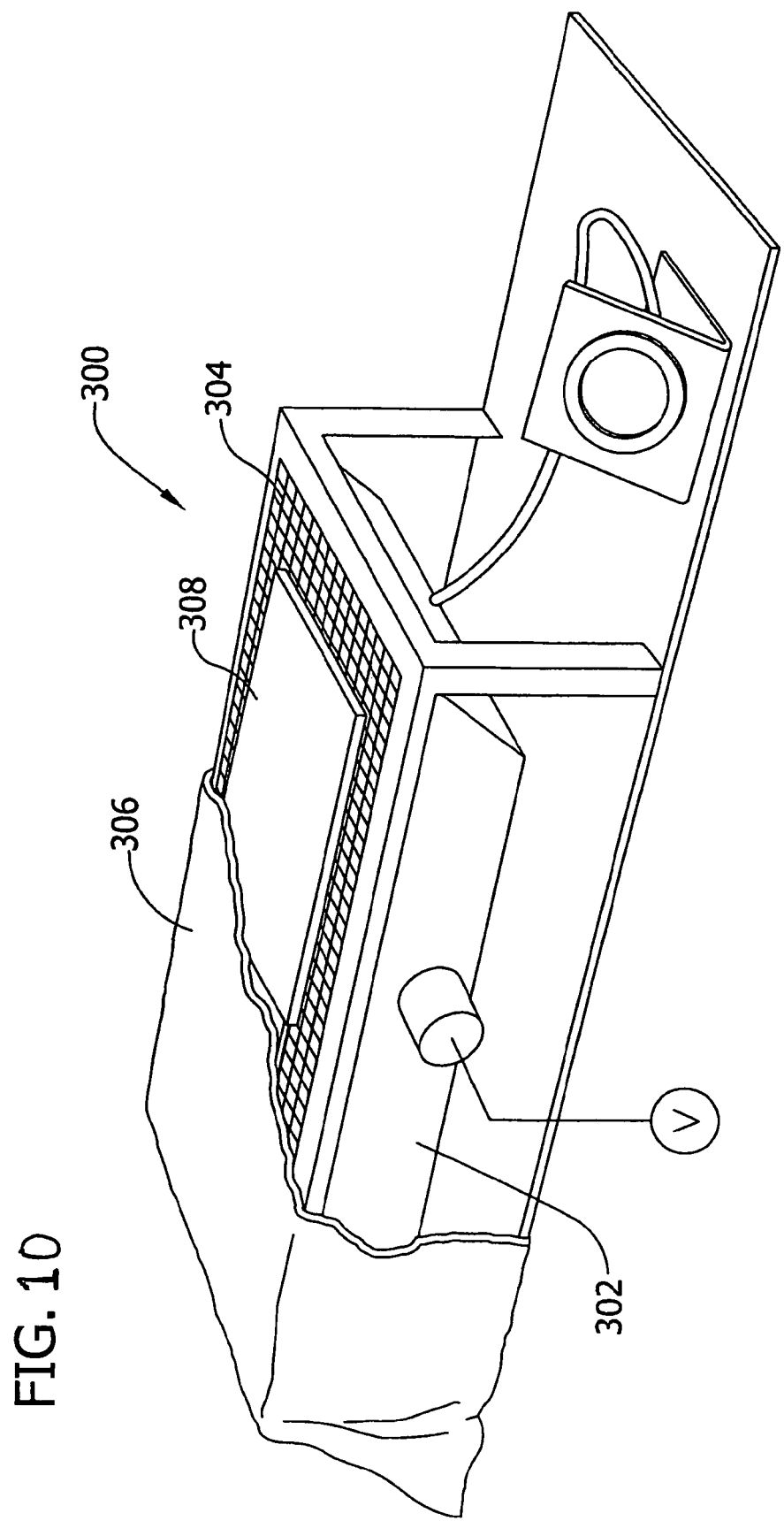
FIG. 10 is a perspective view of apparatus used to conduct the In-Product Planar Growth Test, with portions cut away to show underlying detail.

The following In-Product Planar Growth Test can be used to examine the planar growth characteristics of an absorbent article. FIG. 10 illustrates portions of the apparatus used in conjunction with this Test.

1. Lay flat the absorbent article to be tested such that the liner lies in one plane and the outer cover lies in another plane, relatively parallel to the liner. If the article is in a prefastened, pant-like configuration, open the article (e.g., tear or unfasten side seams, unfasten closure tabs, etc.) so that the article can be laid flat.
2. Snip or remove any active elastic members within or on the test article that prevent the article from lying flat (leg band elastics, containment flaps, waistband elastics, etc.), without substantially disrupting the enclosure of the absorbent core within the chassis.
3. Spread/lay the test article as flat as possible.
4. Measure and record the dry length of the absorbent core at the longitudinal centerline of the absorbent, as well as at positions halfway between the centerline and the side edge of the absorbent at its narrowest point. A permanent marker should be used to mark these three transverse positions for reference later in the test procedure, such that the mark bleeds through the liner onto the absorbent core.
5. Measure and record the dry width of the absorbent at the lateral centerline of the absorbent core, as well as at positions one inch in the longitudinal direction from each end of the absorbent core. A permanent marker should be used to mark these longitudinal positions for reference later in the test procedure, such that the mark bleeds through the liner onto the absorbent core.
6. Using a container with dimensions that are at least those of the dry length and width of the absorbent core of the test article, fill the container with at least 5 liters of 0.9% NaCl solution per product tested, at approximately room temperature (i.e., approximately 23 degrees Celcius).
7. Place the test article into the saline bath with the liner side facing the bottom of the bath.
8. Allow the test article to soak in the saline bath for 20 minutes±0.5 minutes.
9. Remove the test article from the saline bath and place it onto test apparatus, indicated generally at 300 in FIG. 10, comprising a vacuum box 302, a TEFLON fiberglass screen 304 having 0.25 inch (0.6 cm) openings and supported by the vacuum box, and a flexible rubber cover 306 sized for overlaying the screen on the vacuum box. Position the article 308 such that the liner side faces the TEFLON screen.
10. Allow the test article 308 to drain under no pressure for 1 minute.
11. Place the rubber cover 306 over the article 308 and screen 304 (e.g., to generally form a seal over the vacuum box 302) and apply a vacuum (V) of about 0.5 pounds/square inch (about 34.5 dynes/square cm) to the vacuum box (and hence the sample) for a period of about five minutes (5 minutes±0.25 minutes).
12. Remove the test article 308 from the vacuum box, and place on a flat surface with the liner side of the article facing up.
13. Measure and record the wet length of the absorbent core at the same three transverse positions at which the dry length was measured.
14. Measure and record the wet width of the absorbent core at the same three longitudinal positions at which the dry width was measured.
15. Calculate the % growth at each of the three width positions and at each of the three length positions using the formula: % growth=100×((Wet Dimension−Dry Dimension)÷(Dry Dimension))

Modified In-Product Planar Growth Test

The following Modified In-Product Planar Growth Test can likewise be used to examine the planar growth characteristics of an absorbent article. After performing the steps identified above for the In-Product Planar Growth Test, perform the following additional steps:

16. Cut the liner along its longitudinal centerline along the full length of the test article.
17. Near the front and back ends of the test article, cut the liner in the transverse direction, such that the liner can be peeled back to expose the absorbent core.
18. If there are wrinkles or undulations present in the absorbent core, carefully spread/smooth them, without stretching the absorbent, such that the absorbent lays flat. The expanded absorbent core is now unrestricted by the confines of the absorbent chassis.
19. Measure and record the wet length of the absorbent core at the same three transverse positions at which the dry length was measured.
20. Measure and record the wet width of the absorbent core at the same three longitudinal positions at which the dry width was measured.
21. Calculate the % growth at each of the three width positions and each of the three length positions using the formula: % growth=100×((Wet Dimension−Dry Dimension)÷(Dry Dimension))

Active Graphic Test

The following Active Graphic Test can be used to determine if a disposable absorbent article includes a graphic which appears, disappears, partially appears, partially disappears, or is obscured when the article is wetted.

1. Observe the article from both the body-facing surface and the garment-facing surface of the article, making note of which areas include graphics and which areas include no graphics, and making note of the general size and position of any graphics.
2. Lay flat the absorbent article to be tested such that the liner lies in one plane and the outer cover lies in another plane, relatively parallel to the liner. If the article is in a prefastened, pant-like configuration, open the article (e.g., tear or unfasten side seams, unfasten closure tabs, etc.) so that the article can be laid flat.
3. Snip or remove any active elastic members within or on the test article that prevent the article from lying flat (leg band elastics, containment flaps, waistband elastics, etc.), without substantially disrupting the enclosure of the absorbent core within the chassis.
4. Spread/lay the test article as flat as possible.
5. Using a container with dimensions that are at least those of the dry length and width of the absorbent core of the test article, fill the container with at least 5 liters of 0.9% NaCl solution per product tested, at approximately room temperature (i.e., approximately 23 degrees Celcius).
6. Place the test article into the saline bath with the liner side facing the bottom of the bath.
7. Allow the test article to soak in the saline bath for 20 minutes±0.5 minutes.
8. Remove the test article from the saline bath and place it onto test apparatus, indicated generally at 300 in FIG.

10, comprising a vacuum box 302, a TEFLON fiberglass screen 304 having 0.25 inch (0.6 cm) openings and supported by the vacuum box, and a flexible rubber cover 306 sized for overlaying the screen on the vacuum box. Position the article 308 such that the liner side faces the TEFLON screen.

9. Allow the test article 308 to drain under no pressure for 1 minute.
10. Place the rubber cover 306 over the article 308 and screen 304 (e.g., to generally form a seal over the vacuum box 302) and apply a vacuum (V) of about 0.5 pounds/square inch (about 34.5 dynes/square cm) to the vacuum box (and hence the sample) for a period of about five minutes (5 minutes±0.25 minutes).
11. Remove the test article 308 from the vacuum box, and place on a flat surface with the liner side of the article facing up.
12. Note any visible changes to the observations made in Step 1, including the appearance, disappearance, or obscurement of graphics.

EXAMPLES

Prototype training pant chassis containing various components were assembled and tested to examine the impact of various absorbent core configurations on absorbent core planar growth. Each of the prototype chassis included an absorbent core sandwiched between a liquid-permeable liner material and a liquid-impermeable outer cover material. For each chassis, the liner was a 0.3 ounce per square yard (10 grams per square meter) polypropylene spunbond material, neck-stretched 35% to yield a resultant basis weight of 0.4 ounce per square yard, and treated with 0.35% by weight wetting agent; such a material is available from Kimberly-Clark Corporation, Dallas, Tex., U.S.A. For each chassis, the outer cover comprised a stretchable, elastomeric 32 grams per square meter liquid-impermeable film laminated to a 20 grams per square meter extensible polypropylene spunbond. The liner and the outer cover shared the same rectangular dimensions and had a length approximately 2.5 inches longer than the centerline length of the absorbent core 26, and a width approximately 2.5 inches wider that the width of the absorbent core 26 at its widest point.

The chassis of Examples 1-10 contained absorbent cores constituting a substantially homogeneous mixture of approximately 75% superabsorbent material, 10% cellulosic pulp, and 15% polymeric binder, where percentage amounts are by weight. The absorbent core of Example 11 constituted a substantially homogeneous mixture of approximately 63% superabsorbent material and 37% cellulosic pulp. With respect to the cellulosic pulp, codes 1-10 employed Rayonier Sulfatate HJ, available from Rayonier, Jesup, Ga., U.S.A, and code 11 employed NB 480, available from the Weyerhauser Co., Federal Way, Wash., U.S.A.

The Table below lists the superabsorbent polymers and polymeric binders that were used within each prototype. The superabsorbent polymer designated FAVOR SXM 9394 is available from Stockhausen, Inc., Greensboro, N.C., U.S.A. The superabsorbent polymer designated E1231-99 is available from the BASF Corporation, Portsmouth, Va., U.S.A. The polymeric binder designated Kraton G 2755 is available from Kraton Inc., Houston, Tex., U.S.A. The polymeric binders designated Vistamaxx® PLTD 1723 and Vistamaxx® 2210 are available from ExxonMobil Chemical Company, Houston, Tex., U.S.A. Each absorbent core had a thickness of approximately 1.5 millimeters (measured under a pressure of approximately 0.05 pounds per square inch), and defined a generally hourglass shape as representatively illustrated in FIG. 1 by reference numeral 26, where the dry length 54 and front/back width 56 for each code are listed in the Table. The crotch width 58 at the narrowest point of the absorbent core was 60 millimeters for all codes. The absorbent cores had a range of basis weights as indicated in the Table. The basis weight of each absorbent core was generally uniform throughout each core. A process suitable for constructing such absorbent pads is described in U.S. Pat. No. 6,362,389 to McDowall et al. and assigned to Kimberly-Clark Corporation, the contents of which are hereby incorporated by reference to the extent consistent herewith.

The absorbent core was attached to the center of the outer cover via one strip of 6 millimeter wide two-sided adhesive tape centered in the transverse direction 52 on the absorbent and extending the entire length of the chassis. The sealed area 30 of the chassis peripheral area was made by affixing the liner to the outer cover with 12 millimeter wide two-sided adhesive tape adjacent to the perimeters of the liner and outer cover materials. A strip of 6 millimeter wide two-sided adhesive tape was placed between the liner and outer cover, 35 millimeters transversely inward from each side edge of the chassis; these two strips of tape extended the entire length of the chassis and extended over and were affixed to regions of the hourglass-shaped absorbent core that extended within 35 millimeters of the side edges of the chassis.

The planar growth attributes of each code were measured using the Modified In-Product Planar Growth Test described below, with the exceptions that (1) the longitudinal growth of the core was measured only at the centerline position (as opposed to three transverse positions as specified in the Test), and (2) the transverse growth of the core was measured only at a single position 30 millimeters from the front end of the absorbent core (as opposed to three longitudinal positions as specified in the Test).

TABLE

| Ex. | Superabsorbent material | Elastomeric Polymeric Binder | Basis Wgt. (g/m$^2$) | L (cm) | W (cm) | Longitudinal Planar Growth (%) | Transverse Planar Growth (%) |
|---|---|---|---|---|---|---|---|
| 1 | E1231-99 | PLTD 1723 | 425 | 40.5 | 14.3 | −0.3 | 12.7 |
| 2 | E1231-99 | Kraton | 425 | 40.5 | 14.3 | 22.4 | 61.5 |
| 3 | E1231-99 | PLTD 1778 | 425 | 39.5 | 12.2 | 2.1 | 26.6 |
| 4 | E1231-99 | VM2210 | 425 | 39.5 | 12.2 | 14.5 | 55.2 |
| 5 | FAVOR SXM 9394 | VM2210 | 425 | 39.5 | 12.2 | 17.2 | 31.0 |
| 6 | E1231-99 | VM2210 | 530 | 39.5 | 12.2 | 2.4 | 32.2 |
| 7 | E1231-99 | VM2210 | 475 | 39.5 | 12.2 | 0.2 | 27.6 |
| 8 | E1231-99 | PLTD 1778 | 425 | 39.5 | 12.2 | 33.2 | 23.8 |
| 9 | E1231-99 | VM2210 | 425 | 39.5 | 12.2 | 34.2 | 22.6 |
| 10 | FAVOR SXM 9394 | VM2210 | 425 | 39.5 | 12.2 | 35.1 | 19.7 |

TABLE-continued

| Ex. | Superabsorbent material | Elastomeric Polymeric Binder | Basis Wgt. (g/m²) | L (cm) | W (cm) | Longitudinal Planar Growth (%) | Transverse Planar Growth (%) |
|---|---|---|---|---|---|---|---|
| 11 | FAVOR SXM 9394 | None | 540 | 40.8 | 11.5 | 3.9 | 13.8 |

Having described particular embodiments of the invention in detail, it will be readily apparent that various changes and modifications can be made without departing from the spirit of the invention. All of such changes and modifications are contemplated as being within the scope of the invention as defined by the appended claims and any equivalents thereto.

I claim:

1. A disposable absorbent article defining a front waist end, a back waist end, and a length which extends between the front and back waist ends, the disposable absorbent article comprising:
  a chassis comprising a bodyside liner, an outer cover, and an absorbent core sandwiched between the liner and the outer cover; and
  an active graphic disposed on at least one of the bodyside liner and the outer cover, the active graphic positioned within one of a frontmost 30% and a backmost 30% of the article's length, wherein the graphic is visible through the bodyside liner when the article is in a dry state, and wherein the graphic is adapted to become at least partially obscured by the absorbent core when viewed through the bodyside liner after the article has been treated according to the Active Graphic Test.

2. The disposable absorbent article of claim 1, wherein the active graphic is positioned within at least one of a frontmost 25% and a backmost 25% of the article's length.

3. The disposable absorbent article of claim 1, wherein the active graphic is positioned within at least one of a frontmost 20% and a backmost 20% of the article's length.

4. The disposable absorbent article of claim 1, wherein the active graphic is disposed on a layer of the outer cover.

5. The disposable absorbent article of claim 1, wherein the active graphic is disposed on a layer of the liner.

6. A disposable absorbent article defining a front waist end, a back waist end, and a length which extends between the front and back waist ends, the disposable absorbent article comprising:
  a chassis comprising a bodyside liner, an outer cover, and an absorbent core sandwiched between the liner and the outer cover; and
  an active graphic disposed on at least one of the bodyside liner and the outer cover, the active graphic consisting essentially of insoluble ink.

7. The disposable absorbent article of claim 6, wherein the active graphic is positioned within at least one of a frontmost 25% and a backmost 25% of the article's length.

8. The disposable absorbent article of claim 6, wherein the active graphic is positioned within at least one of a frontmost 20% and a backmost 20% of the article's length.

9. The disposable absorbent article of claim 8, wherein the active graphic is disposed on a layer of the outer cover.

10. The disposable absorbent article of claim 9, wherein the graphic is visible through the bodyside liner when the article is in a dry state, and wherein the graphic is adapted to become at least partially obscured by the absorbent core when viewed through the bodyside liner after the article has been treated according to the Active Graphic Test.

11. The disposable absorbent article of claim 8, wherein the active graphic is disposed on a layer of the liner.

12. The disposable absorbent article of claim 11, wherein the graphic is visible through the outer cover when the article is in a dry state, and wherein the graphic is adapted to become at least partially obscured by the absorbent core when viewed through the outer cover after the article has been treated according to the Active Graphic Test.

13. A disposable absorbent article comprising:
  a chassis comprising a bodyside liner, an outer cover, and an absorbent core sandwiched between the liner and the outer cover; and
  an active graphic disposed on at least one of the liner and the outer cover, the absorbent article adapted to provide for an at least partial disappearance of the active graphic without requiring that the active graphic directly contact liquid or atmosphere to effect the at least partial disappearance.

14. The disposable absorbent article of claim 13, wherein the active graphic is positioned within at least one of a frontmost 25% and a backmost 25% of the article's length.

15. The disposable absorbent article of claim 13 wherein the active graphic is positioned within at least one of frontmost 20% and a backmost 20% of the article's length.

16. The disposable absorbent article of claim 15, wherein the active graphic is disposed on a layer of the outer cover.

17. The disposable absorbent article of claim 16, wherein the graphic is visible through the bodyside liner when the article is in a dry state, and wherein the graphic is at least partially obscured by the absorbent core when viewed through the bodyside liner after the article has been treated according to the Active Graphic Test.

18. The disposable absorbent article of claim 15, wherein the active graphic is disposed on a layer of the liner.

19. The disposable absorbent article of claim 18, wherein the graphic is visible through the outer cover when the article is in a dry state, and wherein the graphic is at least partially obscured by the absorbent core when viewed through the outer cover after the article has been treated according to the Active Graphic Test.

20. A disposable absorbent article defining a front waist end, a back waist end, and a length which extends between the front and back waist ends, the disposable absorbent article comprising:
  a chassis comprising a bodyside liner, an outer cover, and an absorbent core sandwiched between the liner and the outer cover; and
  an active graphic disposed on at least one of the bodyside liner and the outer cover, wherein the graphic is visible through the bodyside liner when the article is in a dry state, and wherein the graphic is adapted to become at least partially obscured by the absorbent core when viewed through the bodyside liner after the article receives an insult.

* * * * *